United States Patent [19]
Beier

[11] Patent Number: 4,479,182
[45] Date of Patent: Oct. 23, 1984

[54] DENTAL TREATMENT APPARATUS

[75] Inventor: Stefan Beier, Biberach an der Riss, Fed. Rep. of Germany

[73] Assignee: Kaltenbach & Voigt GmbH & Co., Biberach, Fed. Rep. of Germany

[21] Appl. No.: 358,627

[22] Filed: Mar. 16, 1982

[30] Foreign Application Priority Data

Apr. 7, 1981 [DE] Fed. Rep. of Germany ....... 3114023

[51] Int. Cl.³ .................... G06F 15/20; A61C 19/02
[52] U.S. Cl. .................................... 364/413; 433/28; 433/101
[58] Field of Search .............. 364/413, 415, 400; 433/25, 27, 28, 98, 99, 100, 101, 229

[56] References Cited

U.S. PATENT DOCUMENTS

| | | | |
|---|---|---|---|
| 3,989,952 | 11/1976 | Hohmann | 433/101 X |
| 4,052,649 | 10/1977 | Greenwell et al. | 433/98 X |
| 4,106,198 | 8/1978 | Childress | 433/101 X |
| 4,180,812 | 12/1979 | Kaltenbach et al. | 364/413 X |
| 4,305,126 | 12/1981 | Beier et al. | 364/413 |

Primary Examiner—Joseph F. Ruggiero
Attorney, Agent, or Firm—Scully, Scott, Murphy & Presser

[57] ABSTRACT

A dental treatment apparatus comprising at least one dental treatment instrument, a control data store in which certain fixed control data values are stored and from which they can be called-up as and when necessary, and a display device. In order to permit modification of the control data emitted in each case from the control data store, without the need to refer to the display device, a control member is coupled with the control data store and converts the control data emitted in each case from the control data store into corresponding analog voltages, which can be modified by the emission of an analog voltage corresponding to a desired modification, and which act as operating signals for the instruments.

4 Claims, 2 Drawing Figures

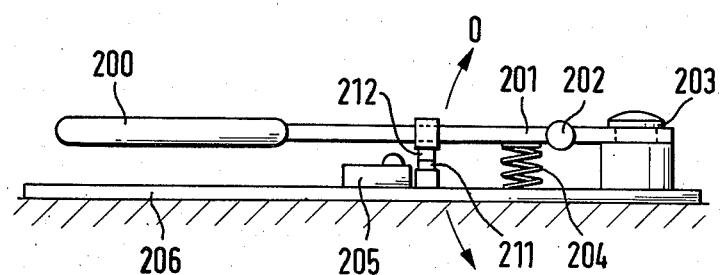
FIG. 2
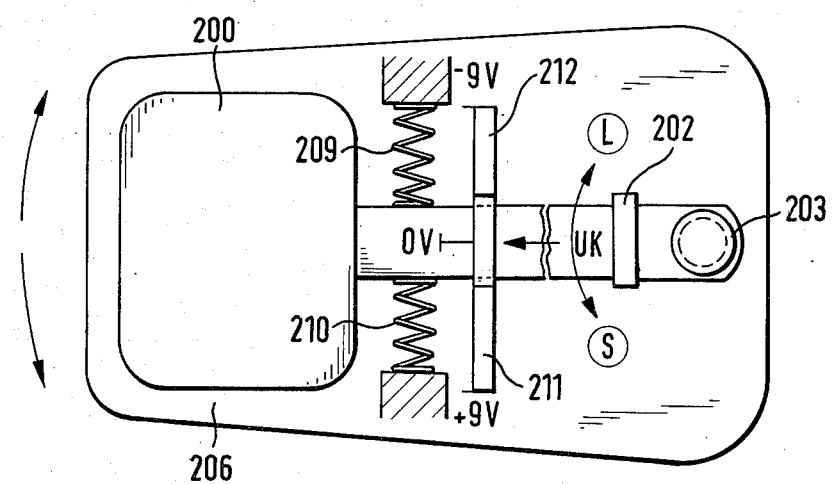

DENTAL TREATMENT APPARATUS

This invention relates to dental treatment apparatus comprising at least one dental treatment instrument, such as a drill, a control data store in which certain fixed control data values, such as certain drill speeds, can be stored and called-up as and when required, and a display device suitable for displaying variable values.

DESCRIPTION OF PRIOR ART

There is disclosed in U.S. Pat. No. 4,180,812 which is assigned to the assignees of the present application, a dental treatment apparatus of the above type, in which a control member for the instrument is coupled to the control data store so that the control data can be varied from the so-called fixed values. The control data store can thereby be set by the control member with instantaneous values of the control data as fixed values to be stored. The display device is suitable for displaying variable values. There is provided between the control member and the display device a data converter, which converts the instantaneous values of the control data into corresponding instantaneous operating data values to be displayed.

With the aid of a dental treatment apparatus of the above type, it is relatively simple for a dentist to store operating data of his own choice as fixed values. When put into operation, the respectively provided treatment instrument starts off with these fixed values. Moreover, the dentist can deviate from the fixed values and vary the operating data. For this purpose, the control member of the relevant treatment apparatus comprises a bidirectional counter, which is coupled to a starter in such a way that the counter can be set into its forwards counting operation or into its backwards counting operation, determining the instantaneous operating data values with its counting positions. This does mean, however, that the adjustment of the control member makes it necessary to observe the display device, since without such observation, there is no definite indication as to the adjustment already carried out of the data supplied by the control data store. At times this is undesirable, particularly when it is a question of making a change in control data supplied in each case by the control data store following the completion of operating processes, during which it is not practically possible to observe the display device.

Accordingly, the present invention seeks to further develop a dental treatment apparatus of the above type, in order to make it possible in a simple manner to vary the control data supplied in each case by the control data store, while avoiding the difficulties pointed out above and without thereby having to pay attention to the provided display device.

According to the invention there is provided dental treatment apparatus comprising at least one dental treatment instrument, such as a drill; a control data store in which certain fixed control data values, such as certain drill speed values, can be stored and can be called-up as and when required; a display device suitable for displaying variable values; a control member for the instrument coupled with the control data store so that the control data can be varied, starting from the so-called fixed values, whereby the control data store can be set by the control member with instantaneous values of control data as fixed values to be stored; and a data converter arranged to convert the instantaneous values of control data into corresponding instantaneous operating data values to be displayed by the display device; in which the control member is arranged to convert the control data emitted in each case by the control data store into corresponding analog voltages, which can be modified by the emission of an analog voltage corresponding to a desired modification, and which act as operating signals for the instrument.

Apparatus according to the invention also has the advantage that the control data emitted in each case from the control data store can be varied relatively simply according to the requirements of each case, without the display device needing to be observed therefor. The analog change or correction effected of the control data emitted in each case from the control data store makes it possible without any further steps to determine the size of a variation or correction value, with which the control data are varied or corrected, by the size of a movement to be carried out. This means that it is possible for a dentist to indicate by touch the completed change to or correction of the said control data, without the visual checking of the display device being necessary.

Advantageously, the amplitude of the analog voltages corresponding to the control data can be modified. This entails the advantage of particularly low expenditure on circuitry to produce the control member.

The control member preferably comprises a digital-analog converter, which is connected to the input side of an adding circuit, whose input side is also connected to a voltage-emitting device, whose voltage emitted in each case may be adjustable in particular with the aid of a foot switch and from whose output the operating signals are derivable, which can be utilised if necessary as new control data. This gives the advantage of particularly low expenditure on circuitry for the assembly of the control member.

The output voltage emitted in each case from the adding circuit is advantageously fed to adjusting members associated with the dental treatment instruments as an analog operating data signal and via an analog-digital converter to the display device as a digital display signal. This gives the advantage that relatively simple devices controllable by analog signals can be used as adjusting members, and that traditional, digitally operated display devices can be used for the display device.

The voltage-emitting device preferably comprises a potentiometer, by whose adjustment the voltage emitted in each case from the voltage-emitting device to the adding circuit is determined. This gives the advantage of only a particularly simple structure being required for the voltage-emitting device. This may be formed by a foot switch with the said potentiometer.

A limiting circuit is preferably connected to the output side of the adding circuit. This measure brings the advantage that the operating signals emitted in each case by the control member can have a value not exceeding a predetermined maximum value, which can be desirable or necessary for safety reasons.

BRIEF DESCRIPTION OF THE DRAWINGS

FIG. 2 shows side and plan views of a foot switch or respectively a foot key for use with a dental treatment apparatus according to the invention.

DESCRIPTION OF PREFERRED EMBODIMENT

Figure 1:
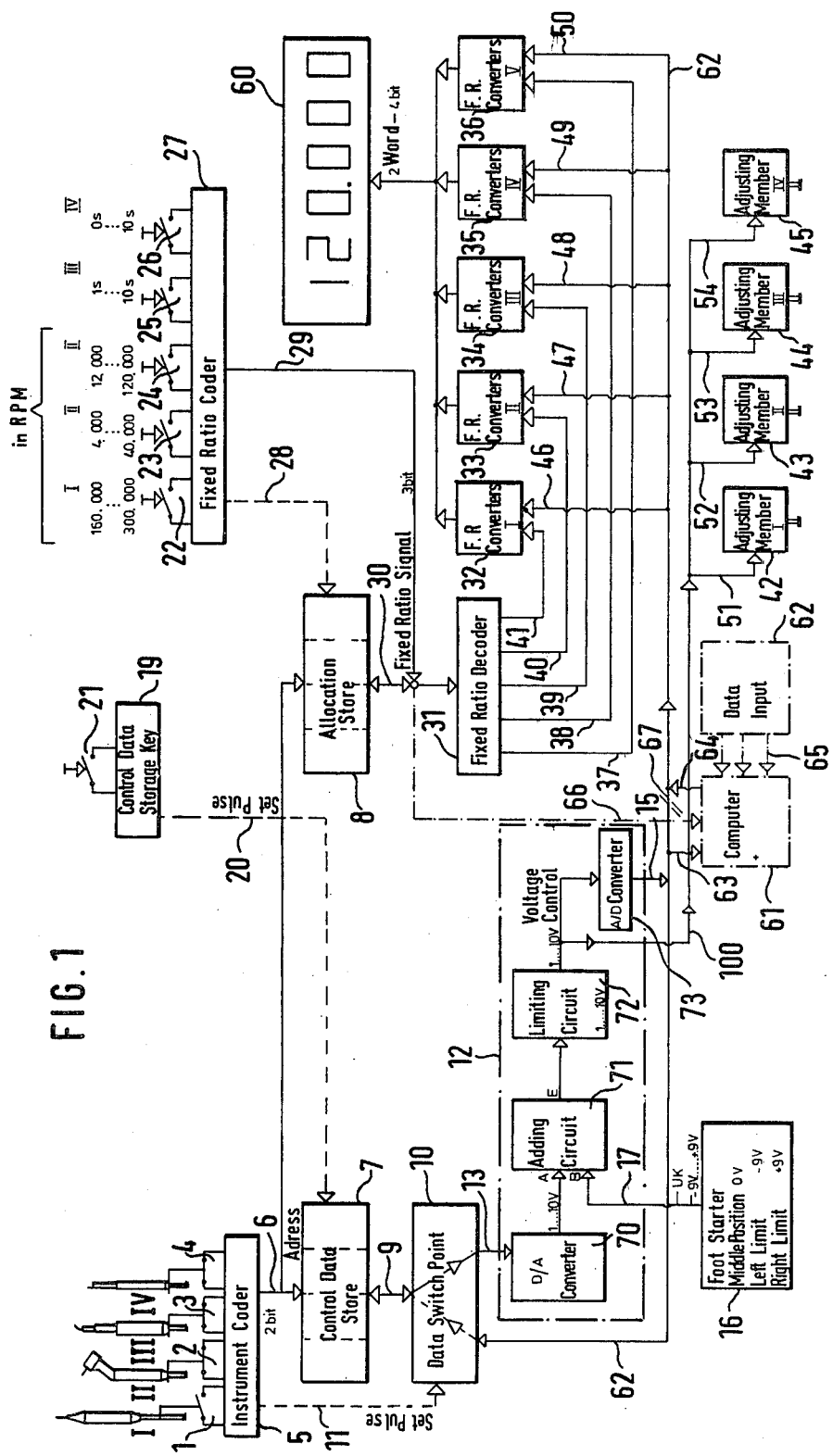
FIG. 1 is a block circuit diagram of a dental treatment apparatus according to the invention.

The block circuit diagram shown in FIG. 1 of a dental treatment apparatus corresponds to a large extent to the block circuit diagram shown in FIG. 1 of U.S. Pat. No. 4,180,812. Treatment instruments I, II, III, IV are provided, with which switches 1, 2, 3, 4 are associated, which are opened when the associated treatment instrument is removed from a holder.

The switches 1, 2, 3, 4 are connected to an instrument coder 5, which can emit via a line 6 an address comprising two bits, indicating the instrument which has just been removed from its holder. The two-bit address in question is fed both to a control data store 7 and to an allocation store 8. These two stores 7, 8 have a number of store registers corresponding to the number of instruments, which in the present case is four respective store registers.

The control data store 7 is connected via a bidirectionally used line 9 to a data switch point 10, to whose one set input a set pulse from the instrument coder 5 is fed via a line 11 when one of the instruments I-IV is removed from its corresponding holder. When such a set pulse occurs the data switch point 10 connects through the data path, via which data signals from the line 9 are passed on from this data switch point 10. In the other setting the data switch point 10 transfers data signals fed to it via the line 9 back to the control data store 7.

The control data store 7 is connected via a line 20 to a control data storage key 19, with which a push-button switch 21 is associated. Operation of this push-button switch 21 sends out a set pulse via the line 20 to the control data store 7. The occurrence of such a set pulse makes it possible for a data signal or an operating signal to be stored in one of the store registers of the control data store 7, which signal is fed directly to this store 7 via the data switch point 10.

The allocation store 8 is connected via a line 28 corresponding to the line 20 to a fixed-ratio coder 27, which is connected to individual switches 22, 23, 24, 25 and 26, by whose operation certain operational value ranges can be determined for the individual instruments I-IV. These value ranges are given in FIG. 1 for the various instruments. It is presumed here that the treatment instrument I is a turbine drill, that treatment instrument II is an electric drill, that treatment instrument III is a plaque remover and treatment instrument IV is a UV-hardener.

The fixed-ratio coder 27 is also connected via a connecting line 29 to a fixed-ratio decoder 31, to which is fed from the fixed-ratio coder 27 a fixed-ratio signal corresponding to the respectively operated key (of keys 22 to 26) in the form of a three-bit signal. This fixed-ratio signal is also fed via the line 30 to the allocation store 8, which permits this three bit signal to be retained in the store register which has just been addressed by a set pulse occurring on the line 28.

Connected to the fixed-ratio decoder 31 via respective output lines 41, 40, 39, 38 and 37 are fixed-ratio converters (translators) 32, 33, 34, 35, 36, which are all connected in common on the output side to a display device 60, to which they permit to be sent in each case two words with four bits respectively. For this purpose, the converters in question 32 to 36 are to be controlled both via the above-mentioned lines 41, 40, 39, 38 and 37, and via further lines 46, 47, 48, 49, 50. These latter lines are connected in common and receive the operating signals, which relate to the treatment instrument used in each case.

These latter-mentioned operating signals are emitted from the control member 12 via a line 62, which is connected both to the lines 46–50 and to one input of the data switch point 10. In the present case, the control member 12 comprises a digital-analog converter 70, whose input is connected via the line 13 to one output of the data switch point 10. The digital-analog converter 70 can be designed in such a way that it can emit from its output an output voltage of between 1 and 10 V. This output voltage is fed to an input side A of an adding circuit 71. Another input side B of this adding circuit 71 is connected via a line 17 to a voltage-emitting device 16, which can comprise in particular a foot starter, which emits a voltage of 0 V in its middle position and voltages of −9 V and +9 V respectively in its two end limit positions. These voltages, which are used to correct the control data emitted in each case from the control data store 7, are processed in the adding circuit with the analog voltage of the control data to form an aggregate signal, which represents the actual operating signal for the respective treatment instrument. This operating signal occurs at the output side E of the adding circuit 71.

According to FIG. 1, a limiting circuit 72 is connected to the output side of the adding circuit 71, which undertakes limitation of the voltages fed to its input side to the range of 1-10 V. This guarantees in a relatively simple manner that signals are emitted from the output of this limiting circuit as operating signals with a voltage whose level does not exceed a fixed level. This voltage level can correspond, for example, to the analog value of the maximum value control data signal contained in the control data store 7.

Connected to the output side of the limiting circuit 72 is an analog-digital converter 73, which converts the regulating voltage (between 1 and 10 V) fed to it from the limiting circuit 72 into a corresponding digital signal. The output side of the analog-digital converter 73 is connected via a line 15 to the above-mentioned line 62. This connection permits feeding of the digital signal emitted in each case from the analog-digital converter 73 both to the fixed-ratio converters 32 to 36, and to the data switch point 10.

Also connected to the output of the limiting circuit 72 of the control member 12 is a line 100, which is connected via individual lines 51, 52, 53, 54 to adjusting members 42, 43, 44, 45, which are associated with the individual treatment instruments I to IV. The analog operating signals emitted in each case from the limiting circuit 72 are fed to these adjusting members via the connecting line 100 for appropriate adjustment.

A computer 61 with an associated programme store arrangement can also be connected to the afore-mentioned line 15 of the analog-digital converter 73 of the control member 12, by means of a line 63. This computer can also be connected with a line 64 to the line 62. In this case, however—as already described in the aforesaid U.S. patent—a dividing point 67 is provided between the input and output of the computer 61. The computer 61 can also be controlled via a line 66, which is connected to the above mentioned lines 29 and 30. Moreover, the computer 61, which can comprise a microprocessor, is connected via lines 65 to a data input 62. The computer 61—which needs to be provided only if necessary, like the data input 62—is used—(as already described in aforesaid U.S. patent)—to vary the operating signals supplied in each case in accordance with further parameters (for example in accordance with the type and size of the respective treatment instrument to be used).

A foot starter is shown in FIG. 2, which is associated with the voltage-emitting device 16 indicated in FIG. 1. This foot starter is built in principle like the foot starter described in the aforesaid U.S. patent. It consists of a foot rest 200, which is secured to the end of a lever 201. The lever 201 is pivotable by means of a first hinge 202 about a horizontal axis and by means of a second hinge 203 about a vertical axis. The second hinge 203 is secured to a base plate 206. By loading the foot rest 200 from above, it can be pressed downwards against the action of a spring 204 supported on the base plate 206, whereby the lever 201 operates a microswitch 205. The latter is used to switch on and off the selected treatment instrument. A slider 212 connected to the lever 201 can be moved on a potentiometer path 211 by lateral deflection of the foot rest 200 against the effect of springs 209, 210, which are supported on parts connected to the base plate 206. The ends of this potentiometer path are connected to voltage terminals, which carry −9 V and +9 V respectively. The relevant potentiometer path 211 is connected to earth at its centre. The lateral deflection of the foot rest 200 thus permits the potentiometer slider 212 to be operated, starting from its central or zero position (0 V), towards the left (L - more slowly) or towards the right (S - more quickly). Voltages between −9 V and +9 V can thereby be derived from the potentiometer slider 212, in accordance with the lateral deflection of the foot rest 200. These voltages are fed to the input side B of the above-mentioned adding circuit 71. The deflection of the foot rest 200 thus makes it simple to modify the output voltage emitted in each case from the digital-analog converter 70 according to FIG. 1. It is also achieved here that the modification of the output voltage emitted from the digital-analog converter 70 and therefore of the control data signal emitted in each case from the control data store 7 according to FIG. 1 is greater, as the deflection of the foot rest 200 from its middle position becomes greater. This means that the amount of adjustment, by which control data emitted from the control data store 7 are modified, is low when the foot rest 200 is deflected by a small amount and greater if it is deflected by a greater amount. This type of modification of the control data emitted in each case from the control data store 7 according to FIG. 1 therefore makes it easy for the dentist administering treatment to carry out adjustment, which entails simple yet reliable recording of the extent of the influence of the control data without any visual checking.

If it is wished to retain the modified control data, emitted from the control member 12 as operating signals, in the control data store 7, it is sufficient—as already described in the aforesaid U.S. patent—to emit a set pulse from the control data storage key 19 via the line 20 to the control data store 7. The control data bits contained in the store register still addressed by the instrument coder 5 are replaced into the store 7 by the data bits fed directly via the data switch point 10 in this store register. These data bits then represent the control data bits emitted by the control data store when it is next appropriately addressed.

Finally it should be noted that the lines mentioned in particular in the context of FIG. 1 may each comprise a plurality of line branches for transmitting the number of signal bits necessary in each case. Furthermore, not only can the described voltage-emitting device 16 be constructed with a potentiometer, as described above, in order to modify the amplitude of the output voltage emitted in each case from the adding circuit 71 or respectively from the limiting circuit 72, but also other quantities of the output voltage in question can also be modified. Thus, when an alternating voltage is emitted from the digital-analog converter 70, its phase position can be shifted by the voltage-emitting device 16 relative to a reference phase position.

I claim:

1. Dental treatment apparatus comprising at least one dental treatment instrument, such as a drill; a control data store in which certain fixed control data values, such as certain drill speed values, are stored and are retrievable when required; a display device suitable for displaying variable values; control means for the instrument being coupled with the control data store for varying of the control data starting from said fixed control data values, the control data store being settable by the control means with instantaneous values of control data as fixed values to be stored; a data converter for converting the instantaneous values of control data into corresponding instantaneous operating data values to be displayed by the display device; said control member converting the control data emitted in each instance by the control data store into corresponding analog voltages, said voltages being modified by the emission of an analog voltage corresponding to a desired modification, and which act as operating signals for the instrument; means for varying the amplitude of the analog voltages corresponding to the control data; and control means comprising a digital-analog converter, an adding circuit having an input side connected to an output of the digital-analog converter, a voltage-emitting device connected to the input side of the adding circuit, and means for adjusting the voltage emitted by the voltage-emitting device, and in which an output of the adding circuit serves as a source from which said operating signals are derived and which forms new control data; a plurality of dental treatment instruments, adjusting members associated each with a respective instrument and being suppliable with the output voltage emitted in each instance from said adding circuit as an analog operating data signal, and an analog digital converter being connected to said adding circuit and being connected to said display device to supply a digital display signal thereto.

2. Dental treatment apparatus according to claim 1, in which said means for adjusting the voltage emitted by the voltage-emitting device comprises a foot-operated switch.

3. Dental treatment apparatus according to claim 1, in which said voltage-emitting device comprises a potentiometer which is adjustable so as to determine the voltage emitted in each case from the voltage-emitting device to the adding circuit.

4. Dental treatment apparatus according to claim 1, including a limiting circuit connected to the output side of said adding circuit.

* * * * *